United States Patent
Roshkovan

(10) Patent No.: US 12,419,752 B2
(45) Date of Patent: Sep. 23, 2025

(54) SURGICAL TECHNIQUE FOR ALVEOLAR RIDGE AUGMENTATION WITH MAXILLARY SINUS ELEVATION (LATERAL APPROACH) USING A PRE-PORTIONED AND READY PRE-PACKAGED BONE GRAFT COMPOSITION IN GELATIN BAG AND METHOD OF PRODUCING IT

(71) Applicant: Igor Roshkovan, Los Angeles, CA (US)

(72) Inventor: Igor Roshkovan, Los Angeles, CA (US)

( * ) Notice: Subject to any disclaimer, the term of this patent is extended or adjusted under 35 U.S.C. 154(b) by 658 days.

(21) Appl. No.: 16/602,715

(22) Filed: Nov. 27, 2019

(65) Prior Publication Data

US 2021/0154015 A1    May 27, 2021

(51) Int. Cl.
*A61L 27/50*    (2006.01)
*A61C 8/00*    (2006.01)
(Continued)

(52) U.S. Cl.
CPC .......... *A61F 2/2803* (2013.01); *A61C 8/0006* (2013.01); *A61C 8/0092* (2013.01); *A61F 2/2846* (2013.01); *A61F 2/3094* (2013.01); *A61F 2/4601* (2013.01); *A61L 27/34* (2013.01); *A61L 27/3608* (2013.01); *A61L 27/365* (2013.01); *A61L 27/3691* (2013.01); *A61L 27/50* (2013.01); *B01J 13/0065* (2013.01); *B01J 13/0069* (2013.01); *A61F 2002/2835* (2013.01); *A61F 2002/2889* (2013.01);
(Continued)

(58) Field of Classification Search
CPC ..... A61C 8/006; A61C 8/0092; A61F 2/2803; A61F 2002/2889; A61F 2002/2835; A61F 2002/2839; A61F 2/4601; A61F 2/2846; A61L 27/34; A61L 27/3608; C08L 89/06
See application file for complete search history.

(56) References Cited

U.S. PATENT DOCUMENTS

| 5,711,315 A | 1/1998 | Jerusalmy |
|---|---|---|
| 7,125,253 B2 | 10/2006 | Kitamura et al. |

(Continued)

FOREIGN PATENT DOCUMENTS

| CN | 110236710 A | * | 9/2019 |
|---|---|---|---|
| EP | 3827850 A1 | | 6/2021 |

(Continued)

OTHER PUBLICATIONS https://www.intechopen.com/chapters/71271 (Year: 2020).*

(Continued)

*Primary Examiner* — Eric J Rosen
*Assistant Examiner* — Luis Ruiz Martin

(57) ABSTRACT

The present embodiment relates generally to methods of performing surgical technique maxillary sinus floor augmentation with a lateral approach using a pre-portioned and ready pre-packaged bone graft composition in gelatin bags and method of producing gelatin bags. In addition the present inventions can be widely used in other medical fields such as dentistry, orthopedic surgery, spine surgery, plastic and reconstruction surgery, sport medicine, trauma surgery, phinoplasty surgery and veterinary.

12 Claims, 15 Drawing Sheets

(51) Int. Cl.
A61C 8/02 (2006.01)
A61F 2/28 (2006.01)
A61F 2/30 (2006.01)
A61F 2/46 (2006.01)
A61L 27/34 (2006.01)
A61L 27/36 (2006.01)
B01J 13/00 (2006.01)

(52) U.S. Cl.
CPC ............ A61F 2002/30064 (2013.01); A61F 2310/00359 (2013.01); A61F 2310/00371 (2013.01); A61F 2310/00383 (2013.01); A61L 2420/02 (2013.01); A61L 2430/12 (2013.01)

(56) References Cited

U.S. PATENT DOCUMENTS

| | | | |
|---|---|---|---|
| 2005/0021142 | A1 | 1/2005 | Ganz et al. |
| 2006/0287732 | A1* | 12/2006 | Pezeshkian ......... A61L 27/3804 623/17.17 |
| 2008/0161934 | A1 | 7/2008 | Yamada |
| 2010/0291511 | A1 | 11/2010 | Lee |
| 2012/0041539 | A1* | 2/2012 | Masters ............... A61L 27/507 623/1.13 |
| 2012/0128774 | A1* | 5/2012 | Lynch .................. A61L 27/12 424/484 |
| 2019/0321514 | A1* | 10/2019 | Pfister ................. A61P 1/02 |

FOREIGN PATENT DOCUMENTS

| | | |
|---|---|---|
| JP | H07 246235 A | 9/1995 |
| WO | 2007/002085 A2 | 1/2007 |
| WO | 2013/192138 A2 | 12/2013 |

OTHER PUBLICATIONS https://www.dentalcare.com/en-us/ce-courses/ce651/normal-radiographic-appearance-supporting-structures (Year: 2022).* https://us.vwr.com/assetsvc/asset/en_US/id/17976164/contents (Year: 2016).* https://www.sciencedirect.com/topics/chemistry/agglomeration#:~:text=Agglomeration%20is%20a%20particle%20formation,food%20processing%20and%20fertilizer%20production. (Year: 2016).*

Misch CE, "Maxillary sinus augmentation for endosteal implants: organized alternative treatment plans" Int J Oral Implantol. 1987; 4(2):49-58.

Zitzmann NU, Naef R, Schärer P., "Resorbable versus nonresorbable membranes in combination with Bio-Oss for guided bone regeneration." Int J Oral Maxillofac Implants Jul.-Aug. 1998;13(4):576.

Silva LD, de Lima VN2, Faverani LP, de Mendonça MR, Okamoto R, Pellizzer EP., "Maxillary sinus lift surgery—with or without graft material? A systematic review." Int J Oral Maxillofac Surg. Dec. 2016; 45(12):1570-1576.

Wallace SS, Froum SJ. "Effect of maxillary sinus augmentation on the survival of endosseous dental implants. A systernatic review," Ann Periodontol. Dec. 2003;8(1):328-43.

Esposito M, Grusovin MG, Rees J, Karasoulos D, Felice P, Alissa R, Worthington H, Coulthard P. "Effectiveness of sinus lift procedures for dental implant rehabilitation: a Cochrane systematic review," Eur J Oral Implantol. 2010 Spring;3(1):7-26.

Esposito M, Felice P, Worthington HV. "Interventions for replacing missing teeth: augmentation procedures of the maxillary sinus," Cochrane Database Syst Rev. May 13, 2014; (5).

Al-Dajani M. "Recent Trends in Sinus Lift Surgery and Their Clinical Implications," Clin Implant Dent Relat Res. Feb. 2016;18(1):204-12.

Ohayon L, Taschieri S, Friedmann A, Del Fabbro. M. "Bone Graft Displacement After Maxillary Sinus Floor Augmentation With or Without Covering Barrier Membrane: A Retrospective Computed Tomographic Image Evaluation," Int J Oral Maxillofac Implants. Dec. 5, 2018.

Al-Dajani M. "Incidence, Risk Factors, and Complications of Schneiderian Membrane Perforation in Sinus Lift Surgery: A Meta-Analysis," Implant Dent. Jun. 2016;25(3):409-15.

EPO Office Action on European Patent Application 20 020 553.2, the patent application of Igor Roshkovan (EP 3 827 850), Jan. 11, 2023.

EPO, Application No. 20020553.2-1109 Intention to grant.

* cited by examiner

SURGICAL TECHNIQUE FOR ALVEOLAR RIDGE AUGMENTATION WITH MAXILLARY SINUS ELEVATION (LATERAL APPROACH) USING A PRE-PORTIONED AND READY PRE-PACKAGED BONE GRAFT COMPOSITION IN GELATIN BAG AND METHOD OF PRODUCING IT

BACKGROUND—PRIOR ART

This disclosure concerns improved dental care for partially edentulous or edentulous patients, and more to a novel methods of performing sinus lift bone augmentation surgery and insertion of dental implants in an alveolar bone of a patient's maxilla jaw during surgery using bone graft in gelatin bag and a method of producing it.

This inventions herein refer to a bone graft, to a technique of making the portioned bone graft composition in gelatin bag and an alveolar ridge augmentation with maxillary sinus elevation (Lateral Approach) surgical method. More specifically, these inventions relate to a new approach of the surgical method for alveolar ridge augmentation with maxillary sinus elevation (lateral approach) using portioned bone graft composition in a gelatin bag and a method of producing it.

The sinus lift augmentation procedure is used to increase the vertical dimension of bone and allow residual bone to accommodate functional dental implants in the atrophic area of the posterior maxilla.

Bone grafting augmentation is a surgical procedure that replaces absent bone matrix with material from patient's own body, an artificial or synthetic and natural substitute. Bone grafting surgical procedure is used because bone tissue has the ability to regenerate partially or completely. As natural bone grows, it mostly replaces the bone grafting material, resulting in a fully integrated augmented area by new bone.

Bone augmentation is a surgical procedure that uses barrier membrane with particulate bone grafts or bone substitutes or mixtures thereof. Typical up-to-date procedures employ a barrier material which is applied over the bone graft.

Moreover, the volume of bone augmentation in sinus lift surgery is difficult to control by a dental provider and causes pain and discomfort for the patient after a surgical procedure and causes a list of postoperative complications.

The following is a tabulation of some prior art that presently appears relevant:

| Pat. No. | Kind Code | Issue Date | Patentee |
|---|---|---|---|
| U.S. Pat. | | | |
| 5,711,315 | A | 1998 Jan. 27 | Jerusalmy |
| 7,125,253 | B2 | 2006 Oct. 24 | Kitamura et al. |
| U.S. Pat. application Pub. | | | |
| 20050021142 | A1 | 2005 Jan. 27 | Ganz et al. |
| 20080161934 | A1 | 2008 Jul. 3 | Yamada |
| 20100291511 | A1 | 2010 Nov. 18 | Lee |

The maxillary sinus is a pyramidal cavity, volume up to 15 mL, contained within the maxillary bone. It is bounded superiorly by the orbital floor, inferiorly by the alveolar process, medially by the lateral nasal wall, and laterally by the zygomatic process and buccal alveolus. The sinus is lined with a thin layer of mucoperiosteum, the Schneiderian membrane, of variable thickness, with an average of approximately 1.0 mm.

Several surgical techniques have been developed to restore the posterior area of maxilla jaw with bone graft. A collagen membrane as a barrier usually placed internally to the sinus, attached to the Schneiderian or sinus membrane, the membranous lining of the maxillary sinus cavity, pushed upside the sinus membrane as the "roof" of the sinus cavity to increase the space for dental implants and help bone to regenerate. This key method described by Misch C E, "Maxillary sinus augmentation for endosteal implants: organized alternative treatment plans" Int J Oral Implantol. 1987; 4(2):49-58.

Bone grafts have been predominantly used to treat bone defects. Many different type of bone materials uses as a bone graft substance such autologous or autogenous bone grafting, allogeneic grafts, xenograft, synthetic substitutes: alloplastic grafts may be made from hydroxyapatites. Bone graft materials are considered for bone tissue regeneration, osteoconduction, hardness of bone and acceptability by human bone.

Moreover in implant dentistry restorable and non resorbable membrane have been used by dental practitioners for over 20 years as barrier membranes.

The resorbable collagen membrane is a well-established biomaterial which used in alveolar ridge augmentation with maxillary sinus elevation (Zitzmann N U, Naef R, Schärer P., "Resorbable versus nonresorbable membranes in combination with Bio-Oss for guided bone regeneration." Int J Oral Maxillofac Implants 1998 July-August; 13(4):576; Silva L D, de Lima VN2, Faverani L P, de Mendonça M R, Okamoto R, Pellizzer E P., "Maxillary sinus lift surgery—with or without graft material? A systematic review." Int J Oral Maxillofac Surg. 2016 December; 45(12):1570-1576; Wallace S S, Froum S J. "Effect of maxillary sinus augmentation on the survival of endosseous dental implants. A systematic review," Ann Periodontol. 2003 December; 8(1): 328-43; Esposito M, Grusovin M G, Rees J, Karasoulos D, Felice P, Alissa R, Worthington H, Coulthard P. "Effectiveness of sinus lift procedures for dental implant rehabilitation: a Cochrane systematic review," Eur J Oral Implantol. 2010 Spring; 3(1):7-26; Esposito M, Felice P, Worthington H V. "Interventions for replacing missing teeth: augmentation procedures of the maxillary sinus," Cochrane Database Syst Rev. 2014 May 13; (5))—incorporated herein by reference).

A dental surgeon may face some intraoperative and postoperative complications during augmentation of the posterior maxilla surgery. Such as sinus or Schneiderian membrane perforation during graft placement, bone graft exposure, postoperative incidences of dislodgement of the bone graft and loss of bone graft (Al-Dajani M. "Recent Trends in Sinus Lift Surgery and Their Clinical Implications," Clin Implant Dent Relat Res. 2016 February; 18(1): 204-12; Ohayon L, Taschieri S, Friedmann A, Del Fabbro M. "Bone Graft Displacement After Maxillary Sinus Floor Augmentation With or Without Covering Barrier Membrane: A Retrospective Computed Tomographic Image Evaluation," Int J Oral Maxillofac Implants. 2018 Dec. 5; Al-Dajani M. "Incidence, Risk Factors, and Complications of Schneiderian Membrane Perforation in Sinus Lift Surgery: A Meta-Analysis," Implant Dent. 2016 June; 25(3): 409-15)—incorporated herein by reference).

There are a potential surgical complications that occur using barrier membrane such as exposure membrane material, infection and difficulty in handling during surgical procedure.

The particles or chips of bone graft coherent mass have a propensity to detach from bone graft carrier during the delivery to surgery site or stick on surface of bone graft carrier.

A new surgical technique for alveolar ridge augmentation with maxillary sinus elevation (lateral approach) using a pre-portioned and ready pre-packaged bone graft composition in gelatin bag and method to make it is presented herein and is destined to make sinus lift surgery easy for a dental surgeon with minimum numbers of complications.

Gelatin is a polypeptide with molecular weight between 15,000 and 249,000 g/mole, which is producing by separating chemicals elements of animal skin and bone collagen.

In an embodiment of these inventions, the portioned bone graft composition can be covered by (or enclosed in a bag of) blood-soluble or saliva-soluble film from collagen derivatives such as collagen or gelatin. Polysaccharides derivatives such as starch, glycogen, and cellulose can also be used.

BRIEF SUMMARY AND OBJECTS OF EMBODIMENT

In reaction to the complications and problems discussed herein, and the present inventions are intended to propose a method that is very effective with less complications surgical technique for alveolar ridge augmentation with maxillary sinus elevation (lateral approach) using a pre-portioned and ready pre-packaged bone graft composition in gelatin bag and method to make it is provided.

The surgical procedure is performed from inside of the mouth cavity of patient where the dental surgeon makes an incision into the soft tissue. After the incision is made, the dental surgeon then pulls back the gum or soft tissue flap, exposing the lateral wall of the sinus in maxilla jaw. Then dental provider creates a "window" in the sinus boney wall. Pulling "window" out or pushing in, the dental surgeon exposes the sinus or Schneiderian membrane and lifts it. The sinus or Schneiderian membrane is detached from the bone, and bone graft material is placed into the recently created space. The gums flap is then sutured close and the graft is left up to 6 months for healing.

During insertion of the bone graft the sinus or Schneiderian membrane can be damaged by sharp particles of bone graft material and because of this bone chips can tighten into the sinus cavity due to the different in atmospheric pressure and spread in the sinus opening.

An advanced aspect of the current inventions are that the bone graft in gelatin bag prevents the displacement bone graft particles from adhering to the walls of gelatin bags.

One method that can be used to enhance the stability of the bone graft is to tightly pack the graft particles.

The ability to keep the appropriate bone space volume is significant during the bone grafting healing process.

One embodiment provides a surgical technique for alveolar ridge augmentation with maxillary sinus elevation (lateral approach) using bone graft composition coated with a blood-soluble film from gelatin and a method of producing gelatin bags with a pre-portioned and ready pre-packaged bone graft composition.

More particularly, the invention related to pre-portioned and ready pre-packaged bone graft in gelatin bags.

In another embodiment the disclosure includes using bone graft material in gelatin bag or other collagen derivatives such as starch or cellulose.

In another preferred invention the portioned bone graft composition can be covered with a blood-soluble film from starch or cellulose and it derivatives.

A single dose of the bone graph composition is placed in bags of blood-soluble gelatin film, preferably made in bone graph chip size by granulation.

In the context of one embodiment the granulation implicates any shaping process which is indicated to particles of predefined size.

In a further embodiment of the disclosure a method of producing gelatin bags for coating pre-portioned bone graft is described.

Moreover an individual portion or individual dose of bone graft modeling by a process called press agglomeration, that is compression bone particles.

Hereby, an individual portion or individual dose of bone graft can be easily dosed and/or mixed with different types of bone graft materials by directly placing the dose in the gelatin bags.

Preferably the process of gelatin preparation starts from blending and heating granulated gelatin and other components in heated warm water in a gelatin melting reservoir. With correct heat level, mixing and vacuum, the components form thick mass combination for use in encapsulation process.

Some other ingredients can be added during the melting process such as surfactants also wetting agents, emulsifying agents, suspending agents.

Moreover, the bone graft preparation or the process of preparing the fill material will be encapsulated. As an encapsulation or the process of transforming the gel mass into a thin layer of gelatin film and wrapping it around the bone grafts forms a pre-portioned and pre-packaged bone graft in gelatin bags.

Preferably, processing reservoirs, mixer apparatus, vacuum homogenizers, sieves and mills, heated and unheated transfer containers, separators may be used for the fill bone graft and gelatin while waiting for encapsulation and can be used to make a portioned bone graft composition in blood-soluble gelatin film bag.

The next step in this process is the drying stage or process which eliminates excess moisture from the gelatin film to shrink and firm up the gelatin bag. Drying occurs by a combination of tumbling and drying.

The bottom gelatin film covers the metal tray with prefabricated concave mold type unit doses, after filing these mold units with bone graft materials a second top gelatin film applied on the top surface of the filled mold type unit doses metal tray.

Afterwards sealing and cutting equipment elements are deployed to create a form of pre-portioned and pre-packaged bone graft in gelatin bags.

An addition, the bone graft particles have different sizes and mixtures comprising different proportion, weight of small and large sizes of bone particles. Particle sizes ranged from a mean of 150-400 microns (mu) as a small size to a large size of up to 1559 mu.

The bags contain blood-soluble gelatin film.

Moreover, gelatin bags will be prepared, pre-portioned and used by dental surgeon.

In one embodiment the gelatin blood-soluble film bag has thickness preferably up to 50 μm.

An addition, the single dose in the bags of blood-soluble gelatin film is preferably heat-sealed by permanently heated sealing element or apparatus.

The present inventions can be widely used in other medical fields such as dentistry, orthopedic surgery, spine surgery, plastic and reconstruction surgery, sport medicine, trauma surgery, phinoplasty surgery and veterinary.

The foregoing advantages and objectives of the present embodiment will be more fully understood upon consideration of the following detailed description of the present invention taken in combination with the selected drawings.

DETAILED DESCRIPTION OF THE PREFERRED EMBODIMENT

Referring to the representation of the images now, the present invention describes a dental surgical technique for maxillary sinus lift and dental implant placement that includes using gelatin bag with a pre-portioned bone graft composition.

In practice, prior to then start of the sinus lift augmentation procedure described above, a current treatment plan must be established based on diagnostic evaluation such as an oral exam, radiographic evaluation from verity radiographs: cone beam computer tomography (CBCT) must be taken to measure the sinus's width and height, panoramic X-ray and full mouth series x-ray is taken to calibrate the patient's upper jaw and maxillary sinuses.

As demonstrated in FIGS. 1 to 15 a method of surgical technique for alveolar ridge augmentation with maxillary sinus elevation (lateral approach) is shown using a bone graft coated by membrane from gelatin and a method of producing coated bone graft according to present.

Figure 1:
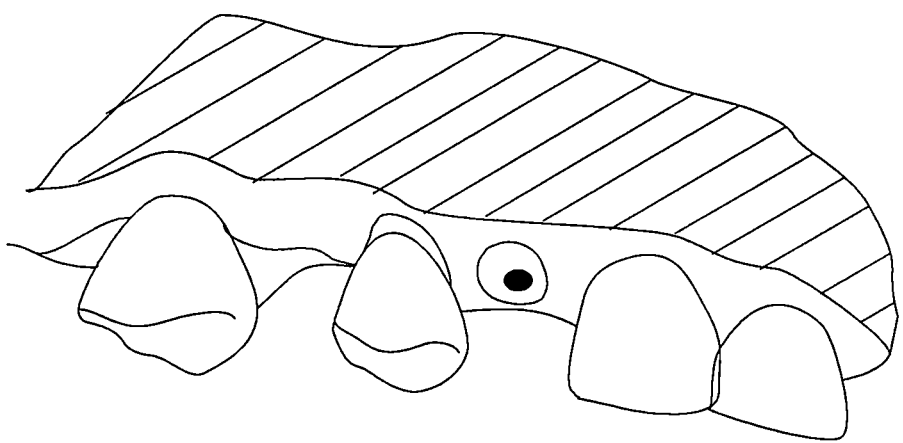
FIG. 1 is a representation of an intra-operative image: pre-operative surgical site.
Figure 2:
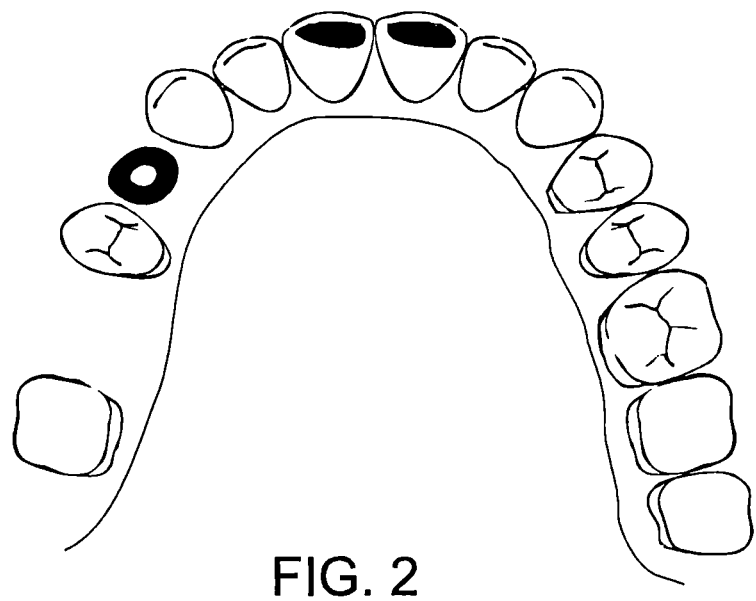
FIG. 2 is a representation of a pre-operative cone-beam computed tomography CBCT of the surgical site—axial view.
Figure 3:
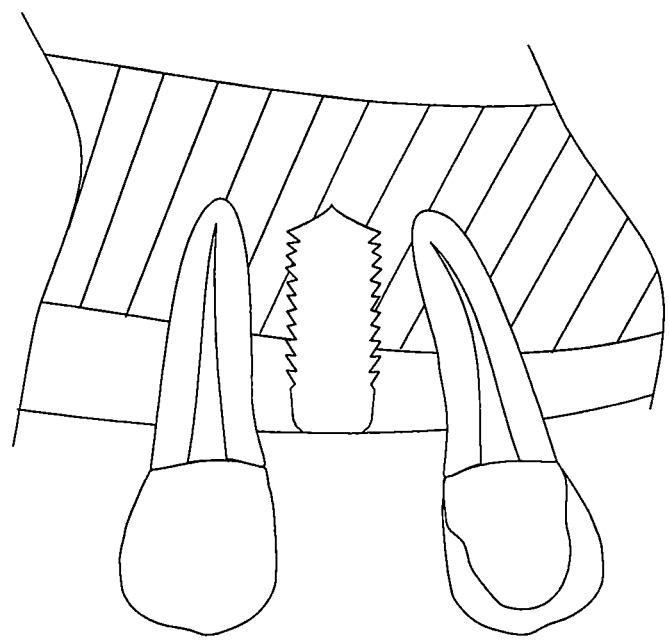
FIG. 3 is a representation of a pre-operative cone-beam computed tomography CBCT of the surgical site—coronal view.

A pre-operative Cone Beam Computed Tomography was performed and used to estimate the efficiency of bone lamina for sinus lifting surgery and bone formation with biomaterials (FIG. 2, 3).

Figure 4:
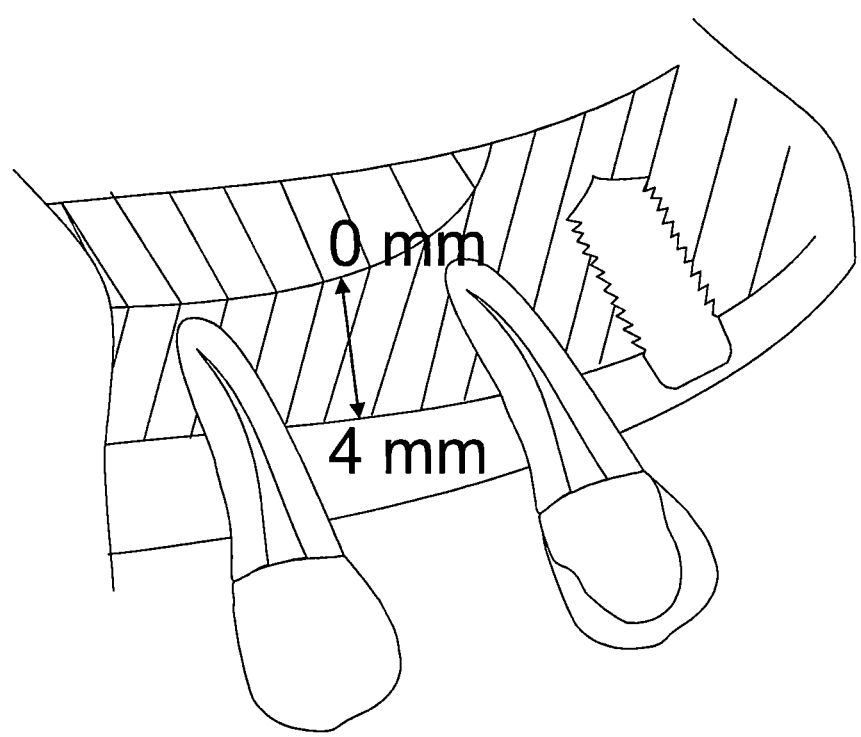
FIG. 4 is a representation of a pre-operative intraoral radiograph of the patient's surgical site with measurements periapical view.

An additional analysis was performed on periapical radiograph (FIG. 4).

Figure 5:
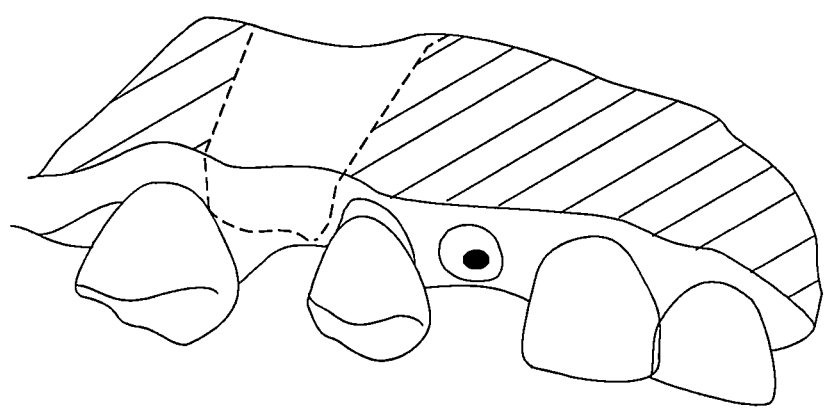
FIG. 5 is a representation of an intra-operative image: initial incision of mucoperiosteal flap design in surgical site.
Figure 6:
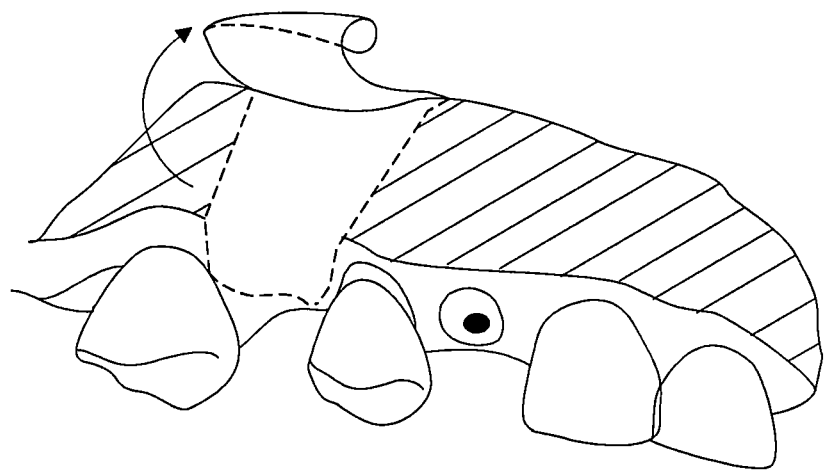
FIG. 6 is a representation of an intra-operative image: the lateral wall of maxillary sinus visualized after raising mucoperiosteal flap.
Figure 7:
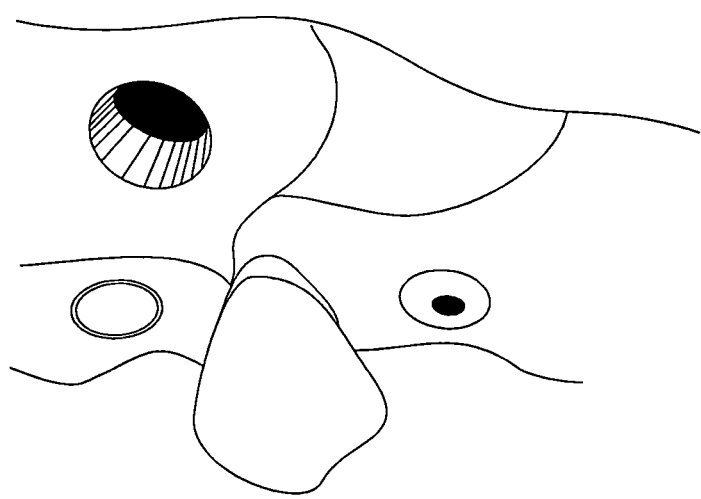
FIG. 7 is a representation of an intra-operative image: osteotomy of the lateral wall of the maxillary sinus.
Figure 8:
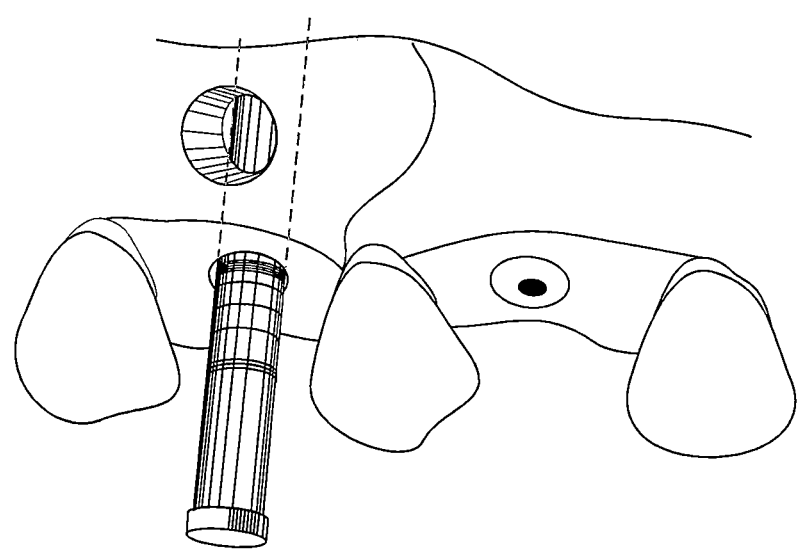
FIG. 8 is a representation of an intra-operative image: lifted maxillary sinus with implant placed.
Figure 13:
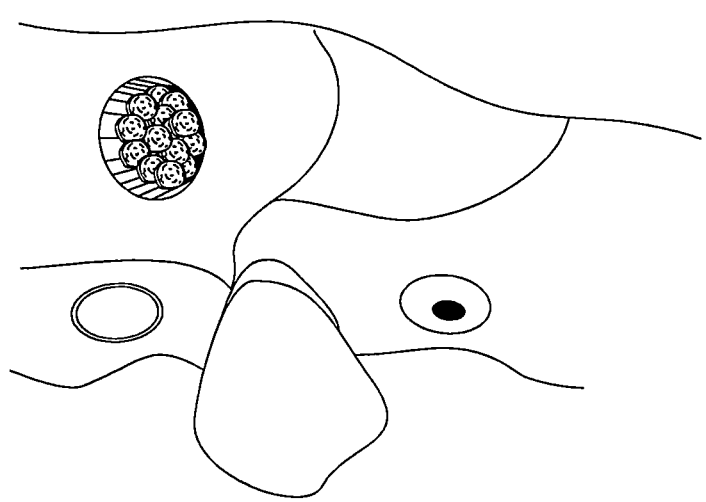
FIG. 13 is a representation of an intra-operative image: maxillary sinus cavity access filled with pre-portioned bone graft composition coated by gelatin bags.
Figure 14:
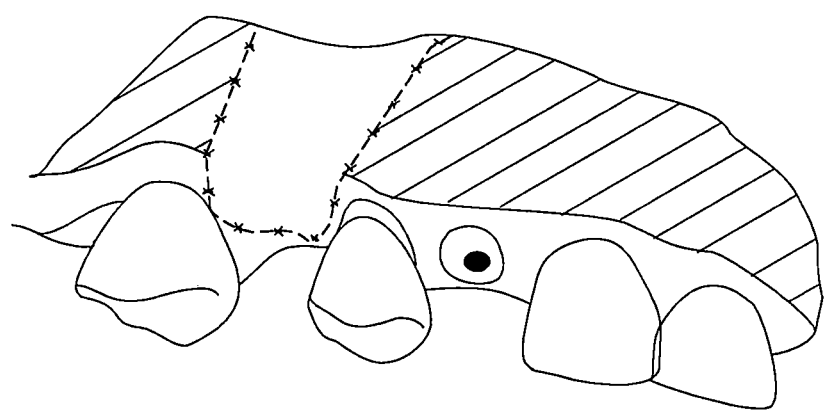
FIG. 14 is a representation of an intra-operative image: buccal view after suturing the flap.
Figure 15:
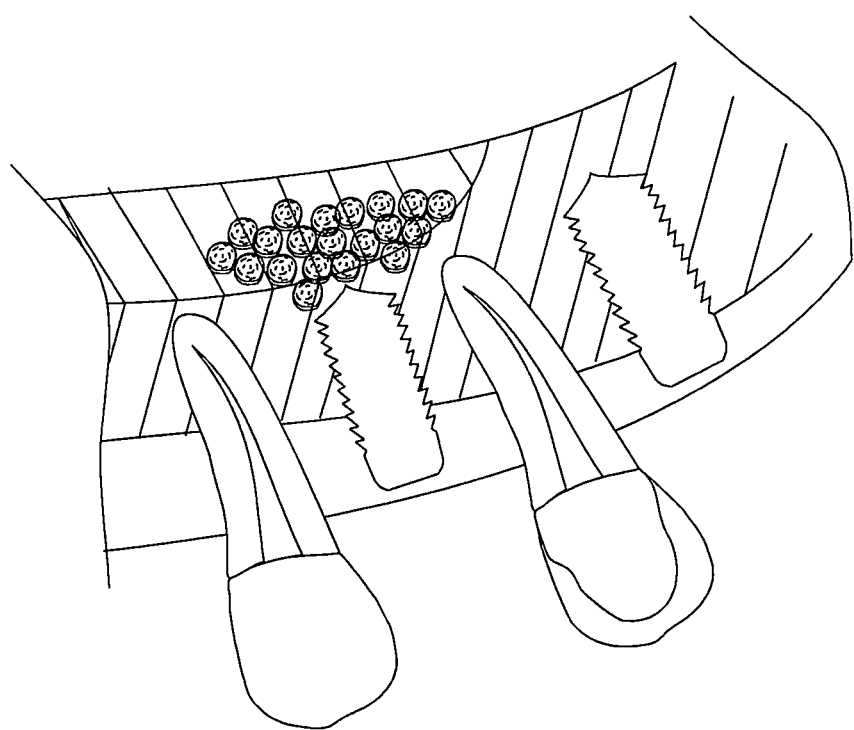
FIG. 15 is a representation of a post-operative intraoral radiograph of the patient's surgical site periapical view showing dental implant in the sinus lift area.

The procedure is performed from inside the oral cavity of patient's mouth (FIG. 1) where the dental provider makes an incision into soft tissue of gingiva (FIG. 5). Once the trapezoid shape incision is performed, the dental surgeon is retracting back the flap of soft tissue to expose the underlying lateral boney wall of the maxillary sinus (FIG. 6). Then the dentist creates an entry to the maxillary sinus, to get access to the sinus or Schneiderian membrane (FIG. 7). The sinus membrane is detached from the bone of the inferior surface of the sinus cavity and the newly formed space within the bony cavity of the maxillary sinus is grafted with pre-portioned and ready pre-packaged bone graft composition in gelatin bags (FIGS. 9-12) to provide sufficient space to place dental implants into the surgical site (FIGS. 8, 13, 15). A root form implant (AB-implant, 4.2×10 mm) was placed and the gums are then sutured close (FIG. 14).

EXAMPLE

The surgical procedure discussed in this case was performed at Privet Dental Office in Los Angeles, California, USA.

A 49-year-old Caucasian female, with a good health status (ASA score: 0), was attended to at the dental office; written informed consent was obtained from the patient to have the case details. Patient was informed regarding the use of a new approach in sinus lift augmentation surgery. She was indicated for a prosthetic implant rehabilitation procedure in the upper right quadrant after a maxillary sinus lift procedure for atrophy of the maxillary bone at the first molar level to install one dental implant.

A pre-operative evaluation of the patient's maxillary sinus for implant planning was performed using CBCT images before surgery, The surgery was performed under antibiotic prophylaxis: Amoxicillin 2 gr 1 hour before the surgery. For the local anesthesia (4% Septocaine with $\frac{1}{100,000}$ epinephrine 1.7 ml 2 cartridges) were administrated in buccal and palatal areas around the tooth. The patient was placed on systemic antibiotics for seven day: Amoxicillin 500 mg (1 capsule every 8 hours).

A full-thickness flap (FIG. 5) was lifted (FIG. 6) via trapezoid shape incision. In the meantime, the receiving site was prepared according to the standard surgical protocol used for lateral sinus floor augmentation (FIG. 7). The wall osteotomy was performed using a slow speed handpiece with a surgical round bur and the window elevation was performed and exposed the underlying Schneiderian membrane (FIG. 8).

Through delicate instrumentation, the sinus membrane was carefully reflected and peeled from the inner surface of the sinus cavity wall (FIG. 8).

A particular mass of bone graft chips can be harvested from different parts of patient jaw or harvested from an individual other than the receiving patient or bone substitutes had its origin from a species other than human or synthetic bone particles.

Figure 9:
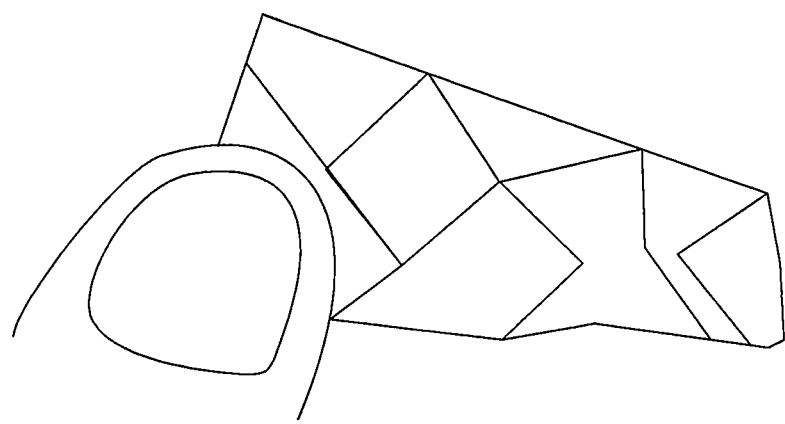
FIG. 9 is a representation of an intra-operative image: gelatin film.
Figure 10:
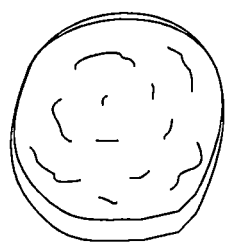
FIG. 10 is a representation of an intra-operative image: preparation bone graft composition coated by film from gelatin.
Figure 11:
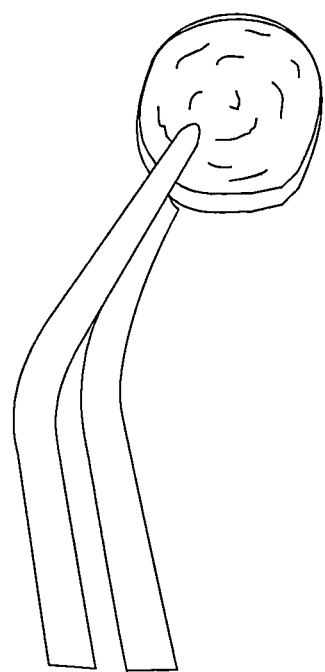
FIG. 11 is a representation of an intra-operative image: gelatin bag with pre-portioned bone graft composition.

At the same time the process to prepare pre-portioned and ready pre-packaged biocompatible osteogenic bone graft composition is started, creating the single dose in the bags of blood-soluble gelatin film (FIGS. 9, 10, 11).

The mass of bone graft consist of a different variety of sizes of bone chips.

The coherent mass of bone graft chips can harvest from cortical, cancellous or mix of both types of bone.

Figure 12:
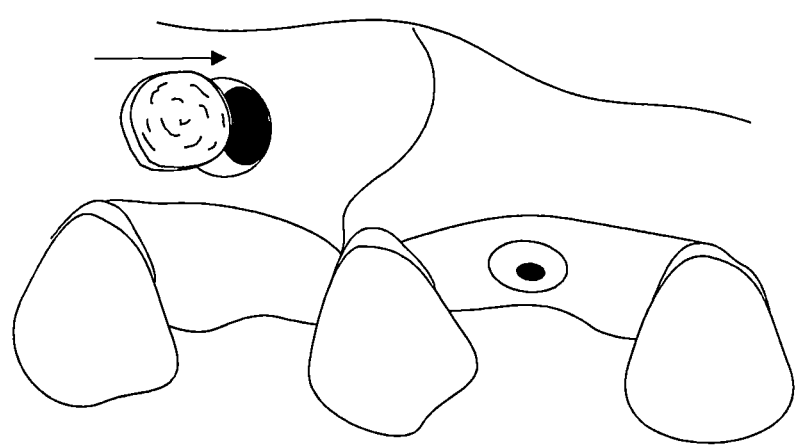
FIG. 12 is a representation of an intra-operative image: the placement the gelatin bag with pre-portioned bone graft composition in the maxillary sinus.

The bone graft was positioned in the newly formed subantral cavity to preserve the sinus membrane, and the space was then filled with the single doses in the bags of blood-soluble and saliva-soluble gelatin film (FIG. 12).

The maxillary sinus entry was packed with gelatin bags (FIG. 13) and the flap was sutured with a 4-0 silk suture and removed ten days post the surgery. (FIG. 14)

A regular size of root form implant (having a 4.2 mm in diameter size and length of 10 mm) was placed (FIG. 15).

The soft tissue around the dental implant healed good with minimal discomfort for patient.

The importance of continuing a high standard of oral hygiene was addressed to the patient.

Tooth brushing and flossing techniques were reinforced.

During the postoperative period, the patient received antibiotic therapy (Amoxillin 500 mg (1 tablet every 8 hours for 7 days) and performed oral rinses with 0.2% Chlorhexidine (Peridex, 0.12%) was prescribed for three times/day for 10 days. (Azizi B, Budimir A, Mehmeti B, Jakovljevid S, Bago I, Gjorgievska E, Gabrio D., "Antimicrobial Efficacy of Photodynamic Therapy and Light-Activated Disinfection Against Bacterial Species on Titanium Dental Implants." Int J Oral Maxillofac Implants. 2018 July/August; 33(4):831-837-incorporated herein by reference).

The prognosis of current surgical procedure was highly favorable. The patient received full explanation regarding long-term prognosis and oral hygiene maintenance. During the time of follow-up no hard and soft tissue changes was detected.

Delayed dental implant placement and delayed loading was planned to allow continue chewing function of the patient.

The surgical technique described in this article developed new approach of alveolar ridge augmentation with maxillary sinus elevation (lateral approach) using a pre-portioned and ready pre-packaged bone graft composition in gelatin bags.

This method eliminates the several commonly found complications such as sinus or Schneiderian membrane perforation, bone graft exposure, postoperative incidences of dislodgement of the bone graft, loss of bone graft and difficulties during manipulation with bone grafting.

Method that can be used to enhance the stability of bone graft for instance, to tightly pack of the graft particles.

Thereby, the above-mentioned discussion discloses and describes simply exemplary embodiments of the present inventions. As doctors will understand, the present inventions can be implemented in other specific forms without changing the main idea of current innovations. Respectively, the disclosure of the present embodiment is planned to be illustrated, but not limiting of the capability of the inventions, as well as other claims.

What is claimed is:

1. A method of treating edentulous patients comprising:
mixing different types of bone graft materials, the bone graft material types consisting of two or more bone graft material types from a list of autologous bone grafting, autogenous bone grafting, allogeneic grafts, xenografts, synthetic substitutes;
placing the bone graft materials on a film, wherein the film has a thickness of up to 50 μm, the film comprising gelatin and a polysaccharide derivative;
sealing the bone graft materials in the film formed into a bag;
making an incision in soft tissue of a patient's mouth cavity;
placing the bag into a space behind the incision; and
suturing the incision.

2. The method of claim 1 further comprising modeling the bone graft materials by press agglomeration.

3. The method of claim 1 wherein the bone graft materials comprises coherent mass bone graft chips harvested from cortical human bone.

4. The method of claim 1 wherein the bone graft materials comprises coherent mass bone graft chips harvested from cancellous human bone.

5. The method of claim 1 wherein the bone graft materials comprises artificial bone graft particles.

6. The method of claim 1 wherein the bone graft materials comprises synthetic bone graft particles.

7. The method of claim 1 further comprising pulling back a soft tissue flap created by the incision, exposing a lateral wall of a sinus in a maxilla jaw.

8. The method of claim 7 further comprising creating a window in a sinus boney wall.

9. The method of claim 8 wherein the bag is placed in the window.

10. The method of claim 1 wherein the polysaccharide derivative is starch.

11. The method of claim 1 wherein the polysaccharide derivative is glycogen.

12. The method of claim 1 wherein the polysaccharide derivative is cellulose.

* * * * *